(12) United States Patent
Coyle et al.

(10) Patent No.: US 7,273,486 B2
(45) Date of Patent: Sep. 25, 2007

(54) CATHETER WITH A CONVERTIBLE PROXIMAL CATHETER SHAFT

(75) Inventors: Noel Coyle, Galway (IE); Patrick Duane, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 672 days.

(21) Appl. No.: 10/411,087

(22) Filed: Apr. 11, 2003

(65) Prior Publication Data

US 2004/0204736 A1    Oct. 14, 2004

(51) Int. Cl.
   *A61M 29/00*   (2006.01)
(52) U.S. Cl. .................... 606/194; 604/103.04
(58) Field of Classification Search .......... 604/43, 604/103.04; 623/1.11; 606/194
   See application file for complete search history.

(56) References Cited

U.S. PATENT DOCUMENTS

| | | | |
|---|---|---|---|
| 4,610,662 A * | 9/1986 | Weikl et al. ............... | 604/509 |
| 4,748,982 A | 6/1988 | Horzewski et al. | |
| 4,762,129 A | 8/1988 | Bonzel | |
| 4,988,356 A | 1/1991 | Crittenden et al. | |
| 5,040,548 A | 8/1991 | Yock | |
| 5,061,273 A | 10/1991 | Yock | |
| 5,149,330 A | 9/1992 | Brightbill | |
| 5,171,222 A | 12/1992 | Euteneuer et al. | |
| 5,178,158 A | 1/1993 | de Toledo | |
| 5,195,978 A * | 3/1993 | Schiffer ...................... | 604/161 |
| 5,205,822 A | 4/1993 | Johnson et al. | |
| 5,217,435 A | 6/1993 | Kring | |
| 5,232,445 A | 8/1993 | Bonzel | |
| 5,263,932 A | 11/1993 | Jang | |
| 5,279,539 A * | 1/1994 | Bohan et al. ............... | 600/37 |
| 5,290,241 A | 3/1994 | Kraus et al. | |
| 5,300,085 A | 4/1994 | Yock | |
| 5,324,269 A | 6/1994 | Miraki | |
| 5,324,296 A * | 6/1994 | Laboureau et al. ........... | 606/88 |
| 5,327,885 A | 7/1994 | Griffith | |
| 5,334,187 A | 8/1994 | Fischell et al. | |
| 5,336,184 A * | 8/1994 | Teirstein ................. | 604/103.04 |
| 5,350,395 A | 9/1994 | Yock | |
| 5,357,978 A | 10/1994 | Turk | |
| 5,364,376 A | 11/1994 | Horzewski et al. | |
| 5,387,226 A | 2/1995 | Miraki | |
| 5,389,087 A | 2/1995 | Miraki | |
| 5,409,459 A | 4/1995 | Gambale | |
| 5,451,233 A | 9/1995 | Yock | |
| 5,458,639 A | 10/1995 | Tsukashima et al. | |
| 5,460,185 A | 10/1995 | Johnson et al. | |
| 5,466,222 A | 11/1995 | Ressemann et al. | |
| 5,489,271 A | 2/1996 | Andersen | |
| 5,496,346 A | 3/1996 | Horzewski et al. | |
| 5,501,227 A | 3/1996 | Yock | |
| 5,531,700 A | 7/1996 | Moore et al. | |
| 5,549,556 A | 8/1996 | Ndondo-Lay et al. | |

(Continued)

*Primary Examiner*—Anhtuan T. Nguyen
*Assistant Examiner*—Elizabeth Houston (57) ABSTRACT

A balloon catheter includes an inflation shaft and an elongated guidewire shaft. A relatively short, distal portion of the guidewire shaft is attached to, or enveloped within, a distal portion of the inflation shaft. A proximal portion of the guidewire shaft is detached from and independent of a proximal portion of the inflation shaft. The detached portion of the guidewire shaft contains perforations at pre-determined points along its length that define removable segments thereof. The removable segments remain attached to the guidewire shaft under normal conditions, but may be torn away from the guidewire shaft to provide access to a guidewire within a guidewire lumen thereof.

12 Claims, 5 Drawing Sheets

U.S. PATENT DOCUMENTS

| | | |
|---|---|---|
| 5,554,118 A * | 9/1996 | Jang ............... 604/102.02 |
| 5,571,094 A | 11/1996 | Sirhan |
| 5,578,009 A | 11/1996 | Kraus et al. |
| 5,626,600 A | 5/1997 | Horzewski et al. |
| 5,685,312 A | 11/1997 | Yock |
| 5,690,642 A * | 11/1997 | Osborne et al. ............ 623/1.11 |
| 5,709,658 A | 1/1998 | Sirhan et al. |
| 5,718,680 A | 2/1998 | Kraus et al. |
| 5,749,888 A | 5/1998 | Yock |
| 5,755,685 A | 5/1998 | Andersen |
| 5,769,868 A | 6/1998 | Yock |
| 5,779,671 A | 7/1998 | Ressemann et al. |
| 5,807,355 A | 9/1998 | Ramzipoor et al. |
| 5,919,164 A | 7/1999 | Andersen |
| 5,919,175 A | 7/1999 | Sirhan |
| 5,947,925 A | 9/1999 | Ashiya et al. |
| 5,947,927 A | 9/1999 | Mertens |
| 6,013,068 A | 1/2000 | Spiegelhalter |
| 6,036,715 A | 3/2000 | Yock |
| 6,056,719 A | 5/2000 | Mickley |
| 6,096,009 A | 8/2000 | Windheuser et al. |
| RE36,857 E | 9/2000 | Euteneuer et al. |
| 6,165,197 A * | 12/2000 | Yock ..................... 606/194 |
| 6,196,995 B1 | 3/2001 | Fagan |
| 6,299,595 B1 | 10/2001 | Dutta et al. |
| 6,569,180 B1 * | 5/2003 | Sirhan et al. ............... 606/194 |
| 6,582,401 B1 * | 6/2003 | Windheuser et al. .. 604/164.05 |
| 6,682,556 B1 * | 1/2004 | Ischinger ................. 623/1.35 |

* cited by examiner

CATHETER WITH A CONVERTIBLE PROXIMAL CATHETER SHAFT

BACKGROUND OF THE INVENTION

1. Field of the Invention

The present invention relates to a medical device. More specifically, the invention relates to a balloon catheter that has an elongated, detached guidewire shaft that may be torn away during catheter exchange.

2. Background of the Invention

Cardiovascular disease, including atherosclerosis, is the leading cause of death in the U.S. One method for treating atherosclerosis and other forms of coronary narrowing is percutaneous transluminal coronary angioplasty, commonly referred to as "angioplasty" or "PTCA". The objective in angioplasty is to enlarge the lumen of the affected coronary artery by radial hydraulic expansion. The procedure is accomplished by inflating a balloon of a balloon catheter within the narrowed lumen of the coronary artery. Radial expansion of the coronary artery occurs in several different dimensions, and is related to the nature of the plaque. Soft, fatty plaque deposits are flattened by the balloon, while hardened deposits are cracked and split to enlarge the lumen.

One or multiple dilations may be necessary to effectively dilate the artery. In many instances, successive dilations using a succession of balloon catheters with balloons of increasingly larger diameters may be required. In order to accomplish the multiple dilations, the original catheter must be removed and a second balloon catheter tracked to the lesion. When catheter exchange is desired, it is advantageous to leave the guidewire in place while the first catheter is removed in order to insert the second catheter without having to reestablish the path by inserting a new guidewire. To remove a balloon catheter while leaving the guidewire in place, there must be a portion of the guidewire extending out of the balloon catheter at the proximal end so that the guidewire can be held in place while the balloon catheter is removed.

Two types of catheters commonly used in angioplasty procedures are referred to as over-the-wire (OTW) catheters and rapid exchange (RX) catheters. A third type of catheter, referred to as a multi-exchange (MX) catheter, is discussed below. An OTW catheter's guidewire shaft runs the entire length of the catheter and is attached to, or enveloped within, an inflation shaft. Thus, the entire length of an OTW catheter is tracked over a guidewire during a PTCA procedure. A RX catheter, on the other hand, has a guidewire shaft that extends within only the distalmost portion of the catheter. Thus during a PTCA procedure only the distalmost portion of a rapid exchange catheter is tracked over a guidewire.

If a catheter exchange is required while using a standard OTW catheter, the user must add an extension onto the proximal end of the guidewire to maintain control of the guidewire, slide the catheter off of the extended guidewire, slide the new catheter onto the guidewire and track back into position. Multiple operators are required to hold the extended guidewire in place while the original catheter is changed out.

A RX catheter avoids the need for multiple operators when changing out the catheter and therefore is often referred to as a "single operator" catheter. With a rapid exchange catheter, the guidewire is outside the shaft of the catheter for all but the distalmost portion of the catheter. The guidewire can be held in place without an extension when the catheter is removed from the body. Once the original catheter is removed, a subsequent catheter may be threaded onto the in-place guidewire and tracked to the lesion. However, one problem associated with RX catheters is that the external portion of the guidewire may become tangled with the catheter shaft during use.

In addition, there are instances when the guidewire and not the catheter must be replaced. For example, the guidewire may become damaged during the procedure or it may be discovered during the procedure that a different shape, length, or size of guidewire is needed. An OTW catheter, with the guidewire lumen extending the entire length of the catheter, allows for simple guidewire exchange. With a RX catheter, the guidewire lumen does not extend the entire length of the catheter. Therefore, current RX catheter designs do not allow for simple guidewire exchange while the catheter remains in place. The guidewire, and most of the catheter, must be removed from the body in order to exchange guidewires. Essentially the procedure must then start anew because both the guidewire and the catheter must be retracked to the treatment site.

A balloon catheter capable of both simple guidewire exchange and catheter exchange without the use of an exchange guidewire is particularly advantageous. A catheter designed to eliminate the need for guidewire extensions or exchange guidewires is disclosed in U.S. Pat. No. 4,988,356 to Crittenden et al., incorporated in its entirety herein by reference. This MX catheter includes a catheter shaft having a cut that extends longitudinally between the proximal end and the distal end of the catheter and that extends radially from the catheter shaft outer surface to the guidewire lumen. A guide member through which the shaft is slidably moveable functions to open the cut such that the guidewire may extend transversely into or out of the guidewire lumen at any location along its length. By moving the shaft with respect to the guide member, the effective over-the-wire length of the MX catheter is adjustable.

When using the MX catheter, the guidewire is maneuvered through the patient's vascular system such that the distal end of the guidewire is positioned across the treatment site. With the guide member positioned near the distal end of the catheter, the proximal end of the guidewire is threaded into the guidewire lumen opening at the distal end of the catheter and through the guide member such that the proximal end of the guidewire protrudes out the proximal end of the guide member. By securing the guide member and the proximal end of the guidewire in a fixed position, the catheter may then be transported over the guidewire by advancing the catheter toward the guide member. In doing so, as the catheter advances toward the guide member, the guidewire lumen envelops the guidewire and the catheter is advanced into the patient's vasculature. In a PTCA embodiment, the MX catheter may be advanced over the guidewire in this manner until the distal end of the catheter having the dilatation balloon is positioned within the stenosis and essentially the entire length of the guidewire is encompassed within the guidewire lumen.

Furthermore, the indwelling MX catheter maybe exchanged with another catheter by reversing the operation described above. To this end, the indwelling catheter may be removed by withdrawing the proximal end of the catheter from the patient while holding the proximal end of the guidewire and the guide member in a fixed position. When the catheter has been withdrawn to the point where the distal end of the cut has reached the guide member, the distal portion of the catheter over the guidewire is of a sufficiently short length that the catheter may be drawn over the proximal end of the guidewire without releasing control of the guidewire or disturbing its position within the patient. After the catheter has been removed, another catheter may be threaded onto the guidewire and advanced over the guidewire in the same manner described above with regard to the MX catheter. The MX catheter not only permits catheter exchange without the use of the very long exchange guidewire and without requiring withdrawal of the initially placed guidewire, but it also overcomes many of the other difficulties discussed in association with RX catheters.

It is among the general objects of the invention to provide an alternative catheter which allows for simple guidewire exchange and fluid delivery. Therefore, what is needed is a catheter design that overcomes the disadvantages set forth above. Specifically, what is needed is a catheter which allows for catheter and/or guidewire exchange without the use of an exchange guidewire, and which avoids the disadvantages associated with prior art catheter designs. Accordingly, there arises a need for an OTW catheter having a detached guidewire shaft which allows for catheter and/or guidewire exchange without the use of an exchange guidewire.

BRIEF SUMMARY OF THE INVENTION

To achieve the foregoing and other objects, and in accordance with the purposes of the present invention as embodied and broadly described herein, the balloon catheter of the present invention provides a balloon catheter capable of catheter exchange without the use of an exchange guidewire while also allowing for simple guidewire exchange. The balloon catheter essentially is comprised of an inflation shaft with an inflation lumen, a guidewire shaft with a guidewire lumen, and a balloon.

The present invention can form the basis of a stent delivery system, as well as an angioplasty catheter. In the present invention, the balloon catheter has an elongated guidewire shaft that acts as a conduit for a guidewire and stretches up to the full length of the balloon catheter. The guidewire shaft's distal portion of a relatively short length is attached to, or enveloped within, the inflation lumen but the remainder of the full length guidewire shaft is detached from the inflation lumen. The detached portion of the guidewire shaft also contains perforations at pre-determined points along its' length that define removable segments of the guidewire shaft. The removable segments remain attached to the guidewire shaft under normal conditions, but may be torn away from the guidewire shaft to provide access to a guidewire within the guidewire lumen as necessary during a procedure.

Further, a balloon is mounted at the distal portion of the inflation shaft. The balloon can be of any shape or size customarily used in angioplasty procedures. The inflation shaft includes an inflation port to allow fluid communication between the inflation lumen and the balloon so that the balloon may be inflated.

The present invention is used in a similar manner to an OTW catheter initially. An extended (two-part) guidewire (approx. 300 centimetres) is tracked to the treatment site. Once in place the balloon catheter of the present invention is slid onto the guidewire and tracked to the treatment site. When a sufficient portion of the extended guidewire protrudes out of the proximal end of the guidewire lumen, the proximal part of the guidewire may be removed, thus shortening the guidewire to the normal, single-user length (approx. 180 centimeters). Alternatively, the balloon catheter may be slid onto a single-user length guidewire outside of the body after which both the guidewire and catheter are tracked into position.

In situ, the guidewire extends the entire length of the catheter within a guidewire shaft. A portion of the guidewire shaft proximal of the balloon is freely detached from the catheter's inflation shaft. Thus, unlike standard RX catheters, the elongated detached proximal guidewire shaft reduces the chance of tangling of the guidewire with the inflation shaft and allows for simple guidewire exchange. To change the guidewire, the user can pull the current guidewire proximally out of the guidewire shaft and feed a new guidewire into the proximal end of the guidewire shaft while the balloon catheter remains in position over the treatment site, as per standard OTW procedure but not currently possible with a RX catheter.

However, unlike standard OTW catheters, the present invention also allows for catheter exchange without the use of an exchange guidewire. With the present invention the user may slide the catheter proximally until the portion of the guidewire which extends externally of the patient is almost entirely within the guidewire lumen. The user then tears-off the most proximal removable segment of the guidewire shaft which exposes more of the guidewire. The catheter is then slid proximally until again the portion of the guidewire which extends externally of the patient is almost entirely covered by the guidewire shaft at which point the user can tear-off the next removable segment of guidewire shaft. This procedure is repeated until the tip of the catheter exits the body and control of the guidewire may be gained distal to the catheter tip and the catheter is fully removed from the guidewire. A new catheter may then be slid over the guidewire.

BRIEF DESCRIPTION OF THE DRAWINGS/FIGURES

The foregoing and other features and advantages of the invention will be apparent from the following, more particular description of a preferred embodiment of the invention, as illustrated in the accompanying drawings.

DETAILED DESCRIPTION OF THE INVENTION

A preferred embodiment of the present invention is now described with reference to the figures, where like reference numbers indicate identical or functionally similar elements. Also in the figures, the left most digit of each reference number corresponds to the figure in which the reference number is first used. While specific configurations and arrangements are discussed, it should be understood that this is done for illustrative purposes only. A person skilled in the relevant art will recognize that other configurations and arrangements can be used without departing from the spirit and scope of the invention.

Figure 1:
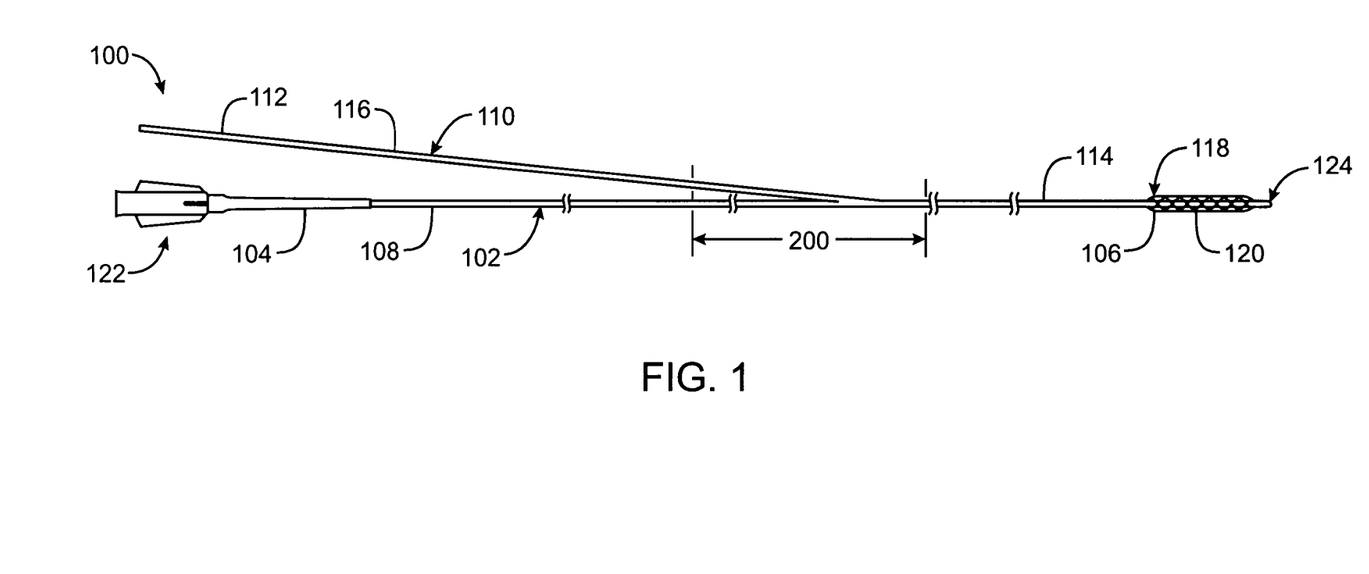
FIG. 1 is a side elevational view of a stent delivery system incorporating the present invention.
Figure 8:
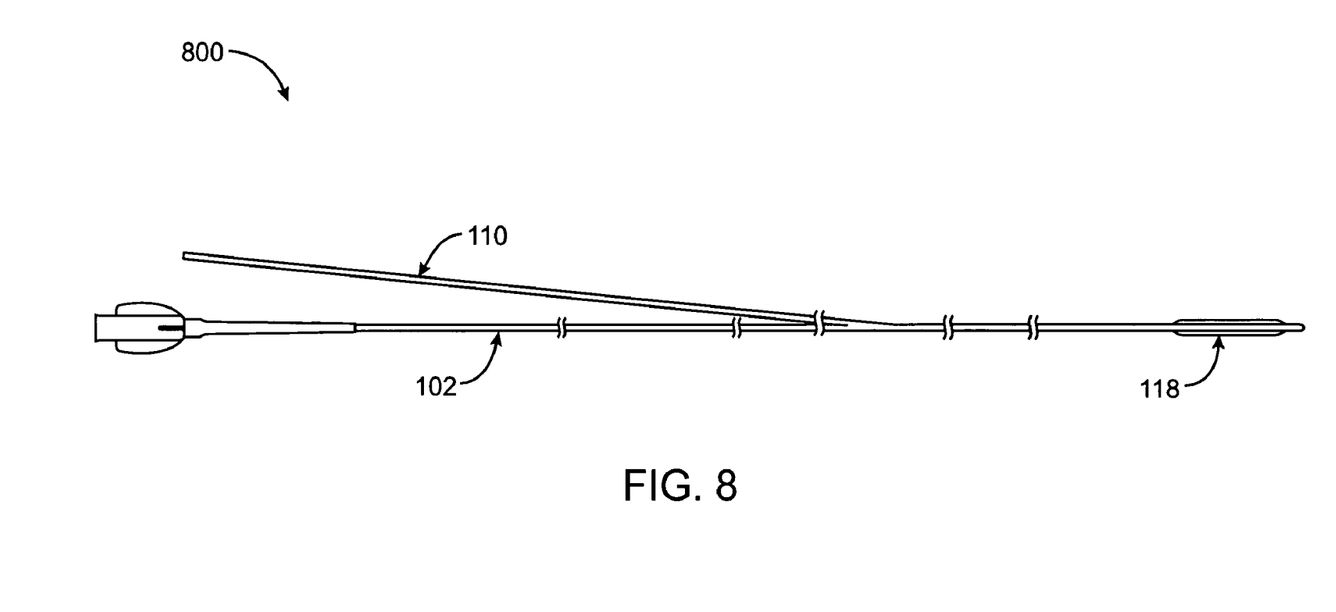
FIG. 8 is a side elevational view of a balloon delivery system incorporating the present invention.

Referring to FIG. 1, an embodiment of a stent delivery system utilizing a catheter according to the present invention is shown. A balloon catheter 100 is provided with an inflation shaft 102, a guidewire shaft 110, and a balloon 118. Inflation shaft 102 has a proximal portion 104, a distal portion 106, and an inflation lumen 108 therein. Guidewire shaft 110 has an elongated proximal portion 112, a relatively short distal portion 114, and a guidewire lumen 116 therein. Balloon 118 may be heat welded or glued onto distal portion 106 of inflation shaft 102, and the interior of balloon 118 is in fluid communication with inflation lumen 108. Proximal portion 104 of inflation shaft 102 is in fluid communication with a hub 122 that allows inflation means (not shown) to be connected thereto for inflation of balloon 118. In addition, stent 120 is located on balloon 118. Catheter 100 is shown as a stent delivery system in FIG. 1, but may be used in balloon angioplasty and/or drug delivery procedures. FIG. 8 shows a balloon catheter 800, an embodiment of the present invention utilizing balloon catheter 800 in a balloon angioplasty procedure.

Inflation shaft 102 is made of any appropriate polymeric material. Possible materials used in construction of inflation shaft 102 are polyethylene terephalate (PET), which allows for very thin walls while withstanding high inflation pressures; nylon, which provides a soft material; and polyethylene, which is advantageous for its compatibility with new angioplasty techniques, such as lasers. The proximal portion of inflation shaft 102 is formed from a reinforced polymeric tube or a metal hypo tube. Guidewire shaft 110 may be made of any appropriate polymeric material. Non-exhaustive examples of material for guidewire shaft 110 include polyethylene, PEBAX, nylon or combinations of any of these, either blended or co-extruded. Preferred materials for inflation shaft 102 and the guidewire shaft 110 are polyethylene, nylon, PEBAX, or co-extrusions of any of these materials. Balloon 118 can be any appropriate shape or size, and any material, which is relatively elastic and deformable. Non-exhaustive examples for balloon 118 include polymers such as polyethylene, PEBAX, PET, nylon, polyurethane.

Guidewire shaft 110 acts as a conduit for a guidewire and stretches up to the full length of balloon catheter 100. Distal portion 114 of guidewire shaft 110 is attached to, or enveloped within, inflation lumen 108. The remainder of full length guidewire shaft 110, i. e., proximal portion 112, is detached from inflation shaft 102. The elongated guidewire shaft 110 allows for simple guidewire exchange. To change a guidewire, the user can pull the current guidewire proximally out of guidewire shaft 110 and feed a new guidewire into the proximal end of guidewire shaft 110 while balloon catheter 100 remains in position within a body lumen, as per standard over-the-wire procedure but not currently possible with a typical rapid exchange catheter. In addition, elongated guidewire shaft 110 prevents the problem of inflation shaft 102 becoming entangled with a guidewire, which may occur during use of typical rapid exchange catheters.

Figure 2:
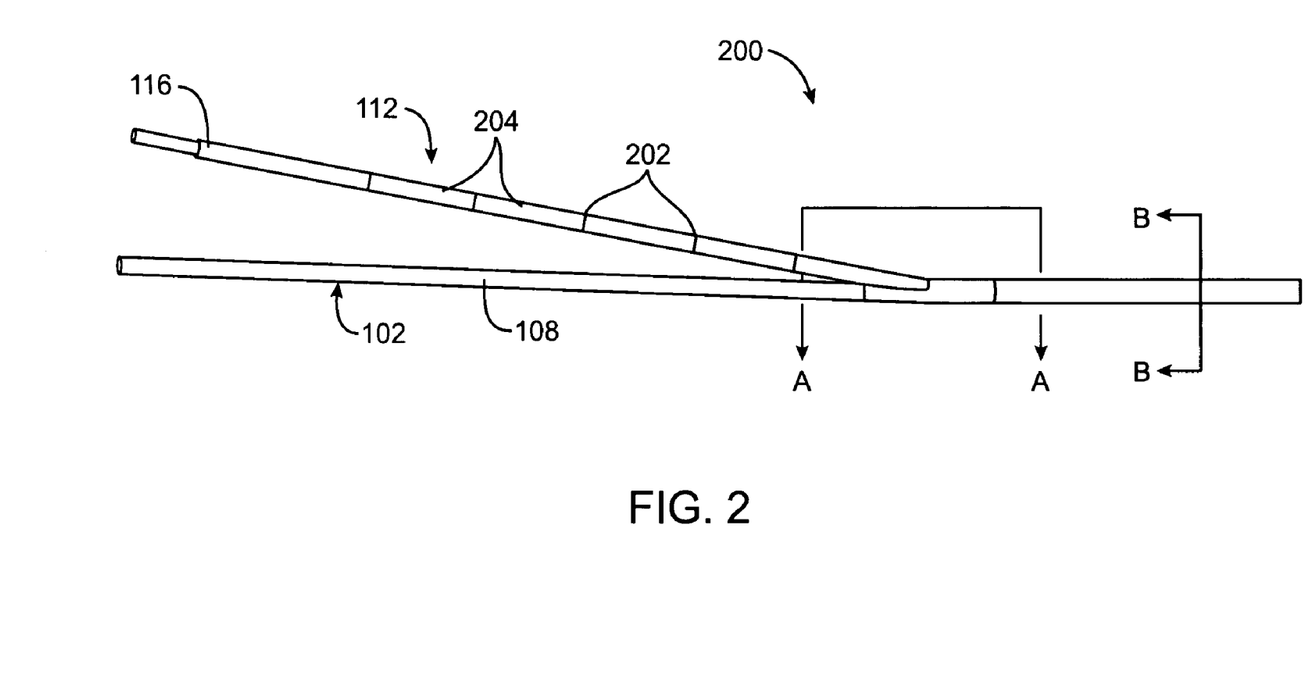
FIG. 2 is an enlarged view of a transition portion 200 of the catheter of FIG. 1.

FIG. 2 is an enlarged view of a transition portion 200 of FIG. 1, and shows the location at which guidewire shaft 110 becomes detached from and independent of inflation shaft 102. As shown in FIG. 2, proximal portion 112 of guidewire shaft 110, which is detached from inflation shaft 102, also includes perforations 202 at pre-determined points along its length. Perforations 202 define removable segments 204 along proximal portion 112 of guidewire shaft 110. In one embodiment of the present invention, the perforations may be circumferentially placed about guidewire shaft 110. In another embodiment of the invention, the perforations may extend from an outer surface to an inner surface of proximal portion 112 of guidewire shaft 110 so as to form "slots" therein. Removable segments 204 remain attached as proximal portion 112 of guidewire shaft 110 under normal conditions, but may be torn away, singly or in multiples, from guidewire shaft 110 to provide access to a guidewire disposed therein.

Removable segments 204 allow for catheter exchange without the use of an exchange guidewire. With the present invention the user may slide balloon catheter 100 proximally until the portion of the guidewire extending outside the patient's body is almost entirely covered by proximal portion 112 of guidewire shaft 110. The user then "tears-off" the most proximal removable segment 204 of guidewire shaft 110 thereby exposing more of the guidewire. Balloon catheter 100 is then slid proximally until again the guidewire is almost entirely covered by proximal portion 112 of guidewire shaft 110 at which point the user can tear-off the next removable segment 204 of guidewire shaft 110. This procedure is repeated until a distal tip 124 of catheter 100 exits the body and control of the guidewire may be gained at the point of its entry into the body. Balloon catheter 100 is then slid proximally to be fully removed from the guidewire. A new catheter may then be slid over the guidewire that has remained in position during removal of balloon catheter 100.

Figure 3:
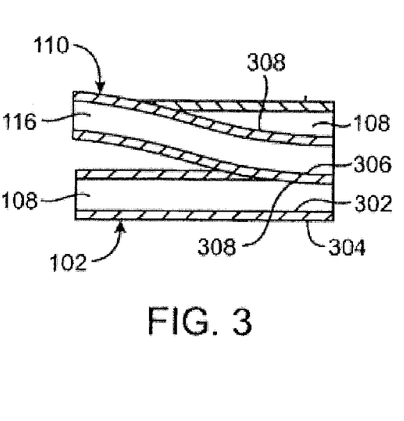
FIG. 3 is a sectional view along line A-A of FIG. 2 in accordance with an embodiment of the present invention.

FIG. 3 is a sectional view at the location along line A-A of FIG. 2, and illustrates an embodiment of transition portion 200 of catheter 100. Transition portion 200 is located proximal of distal tip 124. Transition portion 200 is preferably located, but is not limited to, a distance of between 15 and 28 centimetres proximal of distal tip 124. FIG. 3 illustrates an inner surface 302 and an outer surface 304 of inflation shaft 102, and an inner surface 306 and an outer surface 308 of guidewire shaft 110. In this embodiment of the present invention, distal portion 114 of guidewire shaft 110 is disposed coaxially within inflation shaft 102, with a space between outer surface 308 of guidewire shaft 110 and inner surface 302 of inflation shaft 102 serving as inflation lumen 108 and being in fluid communication with balloon 118. Inflation ports (not shown) are located on inflation shaft 102 to provide fluid communication between an interior of balloon 118 and inflation lumen 108. This embodiment of balloon catheter 100 features guidewire lumen 116 and inflation lumen 108 in a coaxial arrangement. Other embodiments of balloon catheter 100 may have guidewire lumen 116 and inflation lumen 108 in other dual lumen arrangements, such as a circular guidewire lumen above a D-shaped inflation lumen or a circular guidewire lumen set above a crescent-shaped inflation lumen.

Within transition portion 200, at the point where proximal portion 112 of guidewire shaft 110 becomes detached from inflation shaft 102, guidewire shaft 110 generally protrudes externally from outer surface 304 of inflation shaft 102. At this point a bond is formed between the guidewire and inflation shafts to join the shafts and to ensure a smooth transition between the detached proximal portions of the shafts and the joined distal portions of the shafts. Generally, a support mandrel, or wire, is placed within guidewire shaft 110 to traverse the bonding area to ensure that guidewire lumen 116 remains open post bond formation. With the support mandrel remaining within guidewire lumen 116, perforations 202 may be formed using either a single, moveable blade, a 'collet'-type arrangement of numerous blades or by directional laser. After perforations 202 are formed, the support mandrel may be removed.

Figure 4:
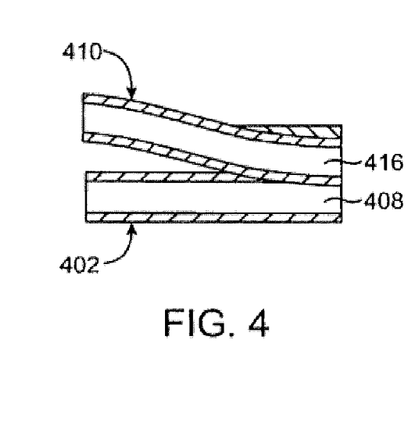
FIG. 4 is a sectional view along line A-A of FIG. 2 in accordance with another embodiment of the present invention.

FIG. 4 is an alternate embodiment along line A-A of FIG. 2, and illustrates another embodiment of transition portion 200 of catheter 100. Alternatively, a guidewire shaft 410 maybe disposed within an inflation shaft 402 in a non-coaxial relationship. This alternate configuration results in a guidewire lumen 416 and an inflation lumen 408 being in a side-by-side arrangement in the distal portion of the catheter.

Figure 5:
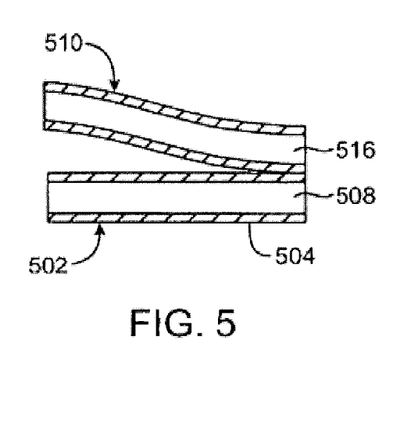
FIG. 5 is a sectional view along line A-A of FIG. 2 in accordance with another embodiment of the present invention.

FIG. 5 is an alternate embodiment along line A-A of FIG. 2, and illustrates another embodiment of transition portion 200 of catheter 100. Alternatively, a guidewire shaft 510 maybe attached to an outside surface 504 of an inflation shaft 502. This alternate configuration has a guidewire lumen 516 and an inflation lumen 508 disposed in a side-by-side relationship in the distal portion of the catheter.

Figure 6:
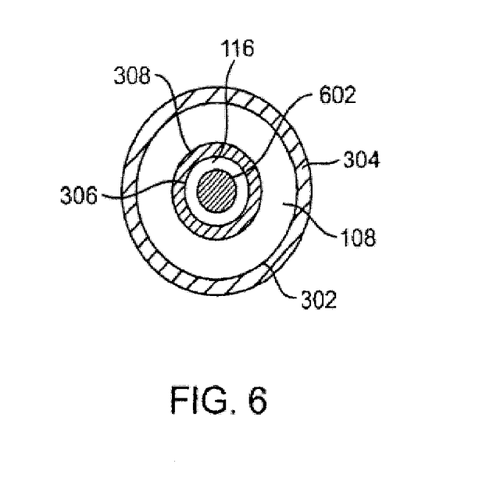
FIG. 6 is a cross-sectional view of a catheter in accordance with an embodiment of the present invention taken along line B-B of FIG. 2.

FIG. 6 is a cross-sectional view of a portion of balloon catheter 100 taken along line B-B of FIG. 2, and illustrates a coaxial dual lumen arrangement as discussed with reference to FIG. 3. As apparent in FIG. 6, inflation lumen 108 is formed between outer surface 308 of guidewire shaft 110 and inner surface 302 of inflation shaft 102 to allow inflation media to flow into balloon 118. FIG. 6 shows a guidewire 602 within guidewire lumen 116.

Figure 7:
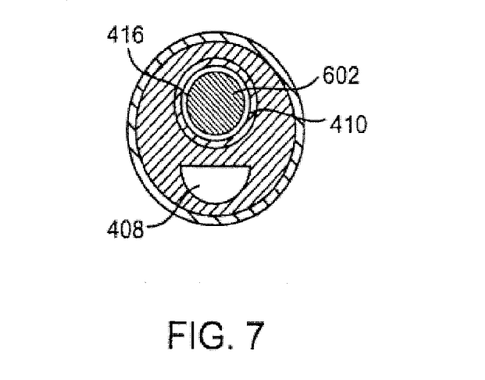
FIG. 7 is a cross-sectional view of a catheter in accordance with another embodiment of the present invention taken along line B-B of FIG. 2.

FIG. 7 is an alternate embodiment of balloon catheter 100 taken along line B-B of FIG. 2, and illustrates a non-coaxial arrangement of guidewire lumen 416 and inflation lumen 408 as discussed with reference to FIG. 4. Guidewire 602 is shown within guidewire shaft 410.

While this invention has been particularly shown and described with reference to preferred embodiments thereof, it will be understood by those skilled in the art that various changes in form and details may be made therein without departing from the spirit and scope of the invention.

What is claimed is:

1. A balloon catheter comprising:
an inflation shaft having a proximal portion, a distal portion, and an inflation lumen;
a guidewire shaft having a proximal portion with perforations that are circumferential around around the guidewire shaft to define removable segments that are detachable from a remainder of the guidewire shaft at the perforations, a distal portion, an outer surface, an inner surface, and a guidewire lumen, wherein the proximal portion of the guidewire shaft is detached from and independent of the proximal portion of the inflation shaft; and
a balloon disposed on the distal portion of the inflation shaft, wherein an interior of the balloon is in fluid communication with the inflation lumen.

2. The balloon catheter of claim 1, wherein the inflation shaft includes an inflation port to provide fluid communication between the interior of the balloon and the inflation lumen.

3. The balloon catheter of claim 1, wherein the distal portion of the guidewire shaft is attached to the distal portion of the inflation shaft.

4. The balloon catheter of claim 3, wherein the distal portion of the guidewire shaft is disposed within the inflation lumen of the distal portion of the inflation shaft.

5. The balloon catheter of claim 1, wherein the guidewire shaft extends substantially the length of the balloon catheter.

6. The balloon catheter of claim 1, wherein the perforations extend from the outer surface to the inner surface of the guidewire shaft.

7. The balloon catheter of claim 1, wherein the removable segments are tubular.

8. The balloon catheter of claim 7, wherein the tubular removable segments are cylindrically shaped.

9. A stent delivery system comprising:
a balloon catheter, the balloon catheter including,
an inflation shaft having a proximal portion, a distal portion, and an inflation lumen;
a guidewire shaft having a proximal portion with perforations defining removable tubular segments thereof, a distal portion, and a guidewire lumen, wherein the proximal portion of the guidewire shaft is detached from the inflation shaft and the removable segments are detachable from the remainder of the guidewire shaft at the perforations to thereby reduce a length of the guidewire lumen; and
a balloon disposed on the inflation shaft, wherein an interior of the balloon is in fluid communication with the inflation lumen; and
a stent mounted on the balloon.

10. A catheter comprising:
a flexible first tube having a proximal portion, a distal portion, an outer surface, and an inner surface;
a flexible second tube having a proximal portion with perforations defining removable tubular segments thereof, a distal portion, an outer surface, and an inner surface, wherein the proximal portion of the second tube is detached from the first tube and the removable tubular segments are detachable from the remainder of the second tube at the perforations.

11. The catheter in claim 10, wherein the distal portion of the flexible second tube is attached to the outer surface of the flexible first tube.

12. The catheter of claim 10, wherein the distal portion of the flexible second tube is enveloped within the flexible first tube.

* * * * *

UNITED STATES PATENT AND TRADEMARK OFFICE
CERTIFICATE OF CORRECTION

| | | |
|---|---|---|
| PATENT NO. | : 7,273,486 B2 | Page 1 of 1 |
| APPLICATION NO. | : 10/411087 | |
| DATED | : September 25, 2007 | |
| INVENTOR(S) | : Noel Coyle et al. | |

It is certified that error appears in the above-identified patent and that said Letters Patent is hereby corrected as shown below:

Column 7, line 42, "rations that are circumferential around around the" should be changed to --rations that are circumferential around the--

Signed and Sealed this

Twenty-first Day of October, 2008

JON W. DUDAS
*Director of the United States Patent and Trademark Office*